(12) United States Patent
Meeranpillai et al.

(10) Patent No.: US 11,852,648 B2
(45) Date of Patent: Dec. 26, 2023

(54) CRUDE OIL DEMULSIFIER CHARACTERIZATION

(71) Applicant: Saudi Arabian Oil Company, Dhahran (SA)

(72) Inventors: Nagoorpitchai S. Meeranpillai, Al-Khobar (SA); Ali Almuhaimeed, Al-Qatif (SA); Osama Alzahrani, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 81 days.

(21) Appl. No.: 17/679,582

(22) Filed: Feb. 24, 2022

(65) Prior Publication Data

US 2023/0266218 A1    Aug. 24, 2023

(51) Int. Cl.
*G01N 9/00*      (2006.01)
*G01N 33/28*     (2006.01)
*G01N 1/38*      (2006.01)
*G01N 13/02*     (2006.01)

(52) U.S. Cl.
CPC ............... *G01N 9/00* (2013.01); *G01N 13/02* (2013.01); *G01N 33/2823* (2013.01); *G01N 1/38* (2013.01)

(58) Field of Classification Search
CPC ....... G01N 9/00; G01N 13/02; G01N 33/2823
See application file for complete search history.

(56) References Cited

U.S. PATENT DOCUMENTS

| | | | |
|---|---|---|---|
| 3,700,335 A | 10/1972 | Seelbinder | |
| 4,876,879 A | 10/1989 | Ruesch | |
| 5,381,002 A | 1/1995 | Morrow et al. | |
| 6,117,682 A | 9/2000 | Lynn et al. | |
| 7,468,402 B2 | 12/2008 | Yang et al. | |
| 8,043,388 B2 | 10/2011 | Waters et al. | |
| 9,285,080 B2 | 3/2016 | Fan et al. | |
| 10,954,455 B1 | 3/2021 | Eggert et al. | |
| 11,262,281 B2 * | 3/2022 | Kokal | G01N 21/85 |
| 2018/0119031 A1 | 5/2018 | Haworth et al. | |
| 2019/0153304 A1 | 5/2019 | Zelenev | |

(Continued)

OTHER PUBLICATIONS

Biolin Scientific ("Sigma 700/701: Attension: Force Tensiometers", https://www.biolinscientific.com/attension/force-tensiometers/sigma-700-701, accessed Jul. 5, 2022.*

(Continued)

*Primary Examiner* — Kristina M Deherrera
*Assistant Examiner* — Jean F Morello
(74) *Attorney, Agent, or Firm* — Fish & Richardson P.C.

(57) ABSTRACT

A sample is placed in a sample housing. The sample includes crude oil and a demulsifier. A cylindrical sensor is submerged in the sample within the sample housing. An external surface of the cylindrical sensor includes a fluoropolymer. A plurality of densities of the sample are measured by a computer for a corresponding plurality of time points over a specified testing time duration. The computer is communicatively coupled to the cylindrical sensor. The plurality of densities and the corresponding plurality of times points are recorded by the computer. An emulsion breaking efficiency of the demulsifier is determined based on the recorded plurality of densities and corresponding plurality of time points.

20 Claims, 5 Drawing Sheets

(56) References Cited

U.S. PATENT DOCUMENTS

2019/0187034 A1 6/2019 Lee et al.
2022/0397522 A1* 12/2022 Thoroddsen ....... G01N 21/3577

OTHER PUBLICATIONS

U.S. Appl. No. 17/550,863, Meeranpillai et al., filed Dec. 14, 2021.
U.S. Appl. No. 17/550,906, Meeranpillai et al., filed Dec. 14, 2021.
U.S. Appl. No. 17/681,406, Meeranpillai, filed Feb. 25, 2022.
U.S. Appl. No. 17/681,576, Meeranpillai et al., filed Feb. 25, 2022.
Banda-Cruz et al., "Crude oil UV spectroscopy and light scattering characterization," Petroleum Science and Technology, Jun. 2016, 34(8):732-738, 7 pages.
Bastow, et al., "Ultraviolet spectroscopy for the analysis of oil-in-water effluent using isopropanol as co-solvent," Applied Spectroscopy, 1997, 51(3):319-322, 5 pages.
Chinaflo.com [online], "Oilfield Chemicals/DRA (Drag Reducing Agent) used for crude oil pipeline transportation, " 2017, retried Oct. 1, 2021, retrieved from URL <https://www.chinafloc.com/DRA-Drag-reducing-agent-used-for-crude-oil-pipeline-transportation_1553.html>, 4 pages.
Civil-instruments-com.sell.everychina.com [online], "Demulsifer Performance Testing Instrument, Petroleum Testing Instrument," 2021, retrieved Oct. 1, 2021, retrief from URL <http://civil-instruments-com.sell.everychina.com/p-106461894-demulsifier-performance-testing-instrument-petroleum-testing-instrument.html>, 2 pages.
Dennington et al., "Miniaturized rotating disc rheometer test for rapid screen of draft reducing marine coatings," Surf. Topog.: Metrol. Prop., Sep. 2015, 10 pages.
Dynetesting.com [online], "Force Tensiometers," May 14, 2014, retrieved on Dec. 9, 2021 from URL <https://dynetesting.com/force-tensiometers/force-tensiometers-sigma-700-701/#squelch-taas-tab-content-0-4>, 8 pages.

Higgins, "Environmentally friendly oil in water analysis by FTIR spectroscopy based on ASTM D7678011," Agilent Technologies, 2012, retrieved from URL <https://www.perlan.com.pl/uploaded/AppBundleEntityProductApplication/fileKey/336/5990-9806enappnote630-4500-5500oilwater.pdf>, 6 pages.
Hong et al., "Rotating disk apparatus for polymer-induced turbulent drafg reduction," Journal of Mechanical Science and Technology, 2008, 22:1908-1913, 6 pages.
Kim et al., "A high-precision rotating disk apparatus for drag reduction characterization," Polymer Testing, 2001, 20:43-48, 6 pages.
Kruss-scientific.com [online], "Force Tensiometer—K100," retrieved on Dec. 9, 2021 from URL <https://www.kruss-scientific.com/en-US/products-services/products/k100?gclid=EAIaIQobChMI08y9yqDk9QIViBTUAR3m0Q7xEAAYASAAEgLIFPD_BwE>, 8 pages.
Kruss-scientific.com [online], "Tensiometer," retrieved on Dec. 9, 2021 from URL <https://www.kruss-scientific.com/en-US/know-how/glossary/tensiometer>, 5 pages.
Lawson-Wood et al., "FT-IR qualtification of hydrocarbons in environmental water samples based on Astm D7678," 2015, retrieved from URL <https://labsense.fi/uploads/7/1/9/5/71957143/ft-ir_quantification_of_hydrocarbons_in_environmental_water_samples_based_on_astm_d7678_012499_01_app.pdf>, 4 pages.
Liquidpower.com [online], "About DRA and How it works," 2021, retrieved Oct. 1, 2021, retrieved from URL <https://www.liquidpower.com/what-is-dra/about-dra-and-how-it-works>, 3 pages.
Schatcogmbh.com [online], "Drag reducing agent (DRA)," retrieved on Feb. 3, 2022 from URL <https://schatcogmbh.com/product/drag-reducing-agent-dra/>, 2 pages.
Spectrosci.com [online], "Techniques for measuring oil in water," 2016, retrieved on Dec. 17, 2021 from URL <https://www.spectrosci.com/knowledge-center/resource-library/oil-in-water-and-soil>, 5 pages.

* cited by examiner

106

106

106

400

CRUDE OIL DEMULSIFIER CHARACTERIZATION

TECHNICAL FIELD

This disclosure relates to characterization of demulsifiers, and in particular, demulsifiers of crude oil.

BACKGROUND

Water occurs naturally in oil and gas wells and reservoirs, for example, from an underlying aquifer or from injector wells, and can mix with and be extracted with the produced hydrocarbons. Co-extraction of water along with mineral hydrocarbons requires expensive separation, treatment, and disposal, which in many cases involves re-injection back into the well. Water cut is the ratio of the quantity of water produced to the total quantity of fluids produced from the production well. As hydrocarbons are depleted from a reservoir, the decrease in reservoir pressure allows for increased water migration into the rock formations, resulting in an increase in water cuts over time. Gas oil separation processes separate produced fluid into gas, oil, and aqueous phases. In some cases, produced water (aqueous phase) is injected back into the subterranean formation, is used in hydraulic fracturing, or is treated and disposed.

SUMMARY

This disclosure describes technologies relating to characterization of demulsifiers of crude oil. Certain aspects of the subject matter described can be implemented as a method. A sample is placed in a sample housing. The sample includes crude oil and a demulsifier. A cylindrical sensor is submerged in the sample within the sample housing. An external surface of the cylindrical sensor includes a fluoropolymer. A plurality of densities of the sample are measured by a computer for a corresponding plurality of time points over a specified testing time duration. The computer is communicatively coupled to the cylindrical sensor. The plurality of densities and the corresponding plurality of times points are recorded by the computer. An emulsion breaking efficiency of the demulsifier is determined based on the recorded plurality of densities and corresponding plurality of time points.

This, and other aspects, can include one or more of the following features. The fluoropolymer can be polytetrafluoroethylene. The entire cylindrical sensor can be made of the fluoropolymer. The cylindrical sensor can include a core. An entire external surface of the core can be coated by the fluoropolymer. The fluoropolymer coating the entire external surface of the core can have a thickness of about 1 millimeter. A plot of the plurality of densities versus the corresponding plurality of time points can be displayed by the computer. The crude oil and the demulsifier can be stirred at a specified stirring rate and for a specified stirring time duration to form the sample prior to placing the sample in the sample housing. The sample can be allowed to rest for a specified resting time duration after placing the sample in the sample housing and prior to submerging the cylindrical sensor in the sample within the sample housing. The sample can be maintained at a specified temperature in a range of from about 75 degrees Fahrenheit (° F.) to about 180° F. while measuring the plurality of densities throughout an entirety of the testing time duration. The specified temperature can be in range of from about 75° F. to about 80° F.

Certain aspects of the subject matter described can be implemented as a system. The system includes a tensiometer and a computer. The tensiometer includes a sample housing and a cylindrical sensor. The sample housing is configured to hold a sample of crude oil and a demulsifier. The cylindrical sensor is configured to be placed within the sample housing. The cylindrical sensor is configured to be submerged in the sample. An external surface of the cylindrical sensor includes a fluoropolymer. The cylindrical sensor is configured to, while submerged in the sample, measure a density of the sample. The computer is communicatively coupled to the cylindrical sensor. The computer includes a processor and a computer-readable storage medium that is coupled to the processor. The computer-readable storage medium stores programming instructions for execution by the processor. The programming instructions instruct the processor to perform operations that include: receiving a plurality of measured densities of the sample from the cylindrical sensor, attributing the plurality of measured densities to a corresponding plurality of time points over a specified time duration, and recording the plurality of measured densities of the sample and the corresponding plurality of time points to the computer-readable storage medium.

This, and other aspects, can include one or more of the following features. The fluoropolymer can be polytetrafluoroethylene. The entire cylindrical sensor can be made of the fluoropolymer. The cylindrical sensor can include a core. An entire external surface of the core can be coated by the fluoropolymer. The fluoropolymer coating the entire external surface of the core can have a thickness of about 1 millimeter. The computer can include an interface. The operations can include displaying, by the interface, a plot of the plurality of densities versus the corresponding plurality of time points. The tensiometer can include a heater that is coupled to the sample housing and communicatively coupled to the computer. The operations can include transmitting a heating signal to the heater to maintain the sample within the sample housing at a specified temperature while the cylindrical sensor measures the plurality of densities throughout an entirety of the testing time duration. The specified temperature can be in a range of from about 75 degrees Fahrenheit (° F.) to about 180° F. The specified temperature can be in a range of from about 75° F. to about 80° F.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes testing of demulsifiers of crude oil. Wet crude is an emulsion of oil (hydrocarbons) and water. Wet crude can be flowed to a gas oil separation unit where phases of the wet crude are separated to produce a dry crude oil product. A demulsifier can be tested for its ability to break an emulsion of crude oil. For example, a demulsifier can be mixed with a sample of crude oil, and the separation of oil and water phases can be characterized to determine the efficacy of the demulsifier.

The subject matter described in this disclosure can be implemented in particular implementations, so as to realize one or more of the following advantages. The apparatuses, systems, and methods described can be implemented to efficiently test demulsifiers for their emulsion breaking capabilities. By implementing the described apparatuses, systems, and methods, an appropriate demulsifier can be selected, which can improve dry crude oil product quality, improve efficiency of gas oil separation processes, and reduce the use of excess demulsifier. Thus, implementation of the described apparatuses, systems, and methods can also result in reduced costs, thereby improving the bottom line of the operator. For example, the apparatuses, systems, and methods described can be implemented to support demulsifier testing operations and produce accurate test results, which can reduce both capital and operating costs associated with implementing demulsifiers in the field.

Figure 1A:
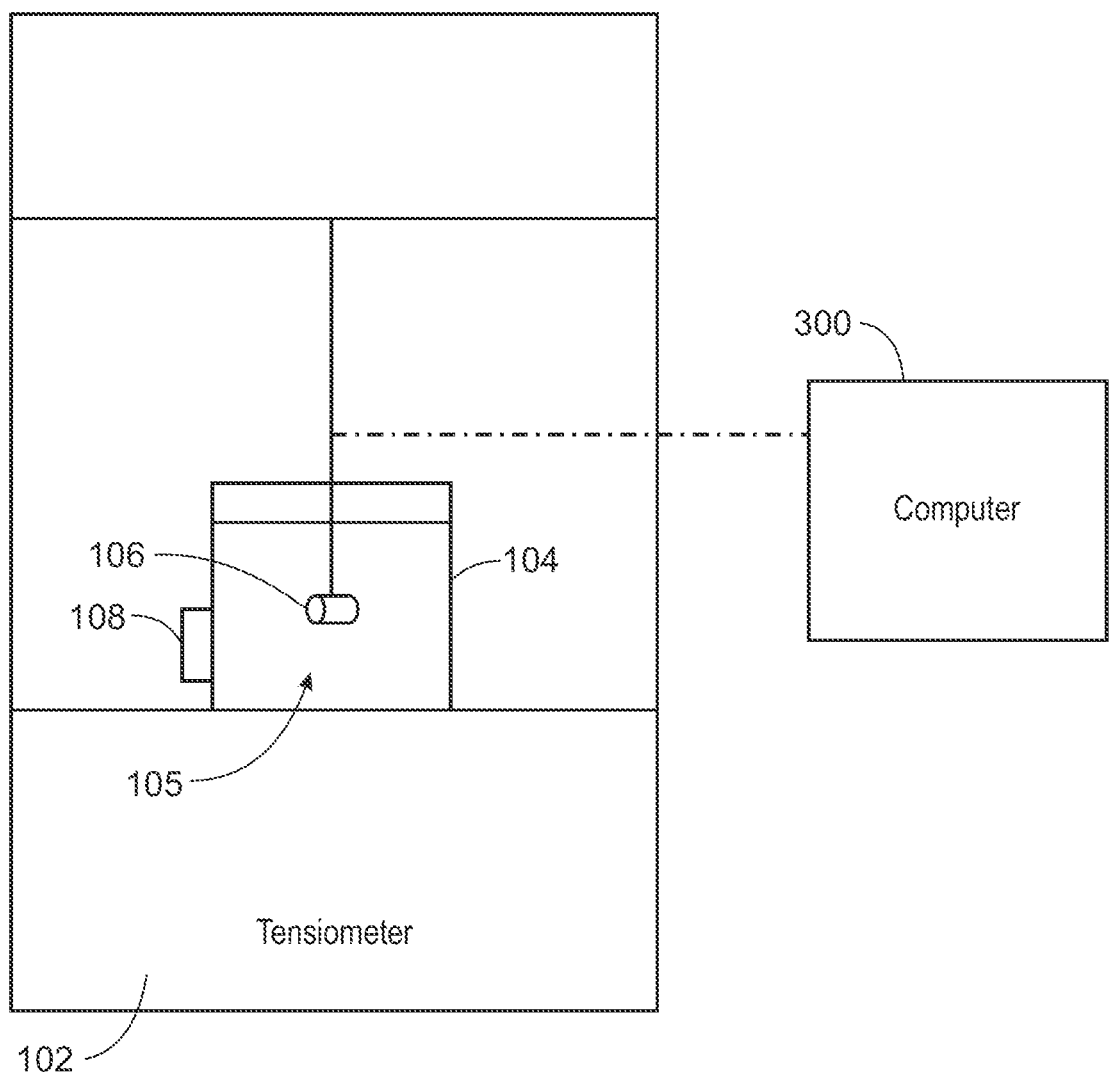
FIG. 1A is a schematic diagram of an example system that can be used to test a demulsifier of crude oil.
Figure 3:
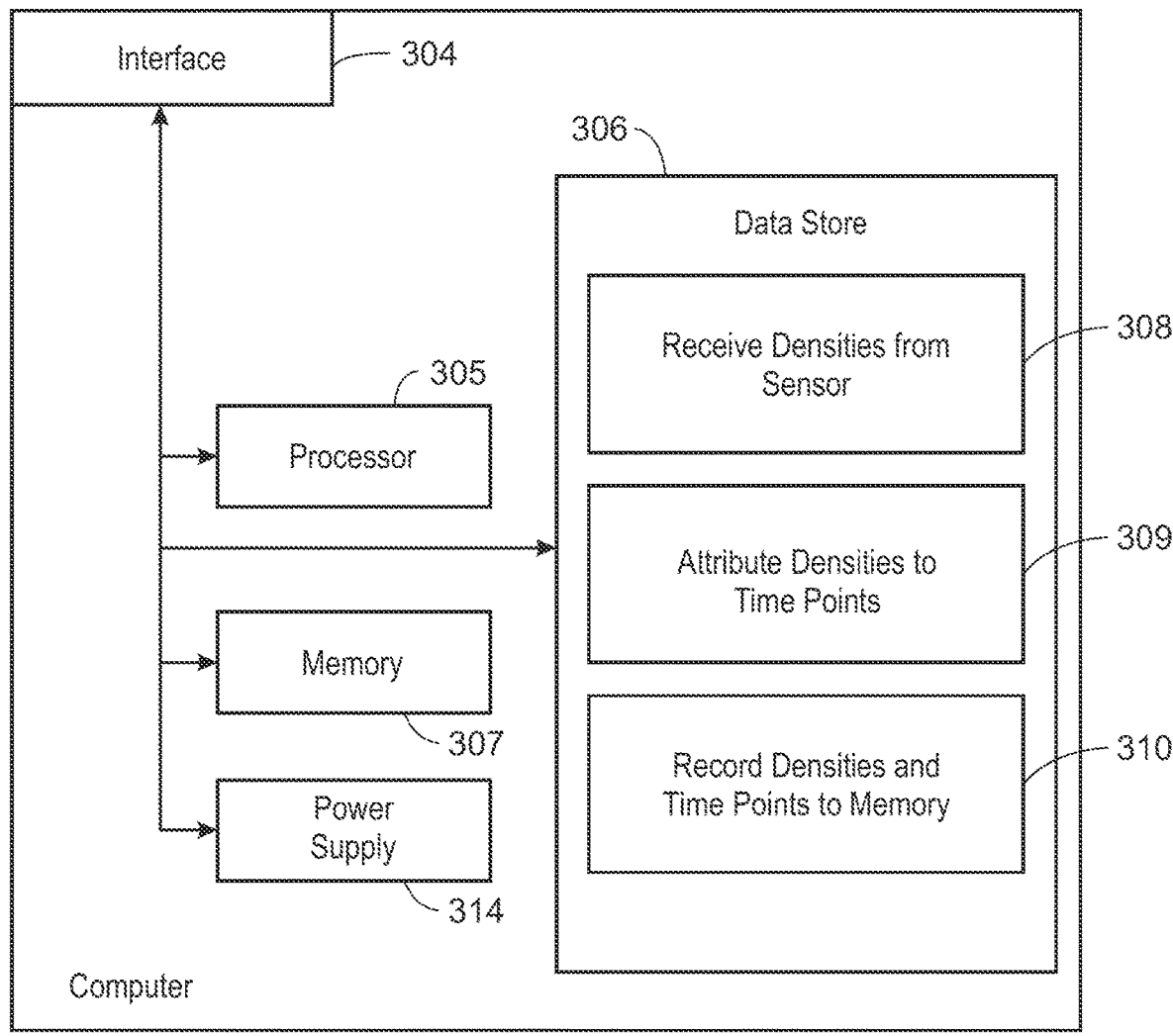
FIG. 3 is a block diagram of an example computer system.

FIG. 1A depicts an example system 100 that can be used to test a demulsifier of crude oil. The system 100 includes a tensiometer 102 and a computer 300. The tensiometer 102 includes a sample housing 104 and a cylindrical sensor 106. The sample housing 104 is configured to hold a sample 105 of crude oil and a demulsifier. The cylindrical sensor 106 is configured to be placed within the sample housing 104. The cylindrical sensor 106 is configured to be submerged in the sample 105. The cylindrical sensor 106 is configured to measure a density of the sample 105 while submerged in the sample 105. The computer 300 is communicatively coupled to the cylindrical sensor 106. The computer 300 is also shown in FIG. 3 and is described in more detail later. The cylindrical sensor 106 and the computer 300 can work together to measure the density of the sample 105 throughout a specified time duration. For example, the cylindrical sensor 106 can measure the density of the sample 105 multiple times throughout the testing time duration. The computer 300 can receive the measured densities of the sample 105 from the cylindrical sensor 106. The computer 300 can attribute the measured densities to corresponding time points over the testing time duration. The computer 300 can record the measured densities and corresponding time points, for example, to memory. The change in density of the sample 105 throughout the testing time duration can be analyzed to determine an emulsion breaking efficiency of the demulsifier. In some implementations, the specified testing time duration is in a range of from about 30 minutes to about 120 minutes. For example, the specified testing time duration can be in a range of from about 50 minutes to about 90 minutes. In some cases, the computer 300 performs the analysis of the demulsifier. In some cases, the computer 300 displays data to a user (for example, in the form of a plot), and the use analyzes the data to determine the emulsion breaking efficiency of the demulsifier.

An external surface of the cylindrical sensor 106 includes a fluoropolymer. The fluoropolymer is made of monomers. Some examples of monomers that can make up the fluoropolymer include perfluorocycloalkene, ethylene, vinyl fluoride, vinylidene fluoride, tetrafluoroethylene, chlorotrifluoroethylene, propylene, hexafluoropropylene, perfluoropropylvinylether, and perfluoromethylvinylether. Fluoropolymers including fluoride-including monomers can exhibit hydrophobicity and is often used in producing non-wetting coatings. Further, fluoropolymers can be resistant to corrosion. Such characteristics can be beneficial for producing sensors for measuring density of crude oil emulsions and for measuring demulsifier performance. Some examples of fluoropolymers include polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluorinated elastomer, fluoroelastomer (such as vinylidene fluoride-based copolymers), tetrafluoroethylene-propylene, perfluoropolyether, perfluorosulfonic acid, perfluoropolyoxetane. In some implementations, the entire cylindrical sensor 106 is made of the fluoropolymer. The cylindrical sensor 106 is sized to fit within the sample housing 104 while being submerged in the sample 105. In some implementations, the diameter of the cylindrical sensor 106 is in a range of from about 10 millimeters (mm) to about 50 mm, from about 20 mm to about 40 mm, or from about 25 mm to about 35 mm. For example, the diameter of the cylindrical sensor 106 is about 30 mm. In some implementations, the length of the cylindrical sensor 106 is in a range of from about 1 mm to about 20 mm, from about 5 mm to about 15 mm, or from about 8 mm to about 12 mm. For example, the length of the cylindrical sensor 106 is about 10 mm. The cylindrical sensor 106 has a density that is greater than the sample 105. For example, the cylindrical sensor 106 has a density that is greater than crude oil. In some implementations, the cylindrical sensor 106 has a density in a range of from about 1 gram per cubic centimeter ($g/cm^3$) to about 5 $g/cm^3$ or from about 2 $g/cm^3$ to about 4 $g/cm^3$. For example, the cylindrical sensor 106 has a density of about 2 $g/cm^3$.

The tensiometer 102 can include a heater 108. The heater 108 can be coupled to the sample housing 104. The heater 108 is configured to maintain the sample 105 within the sample housing 104 at a specified temperature while the cylindrical sensor 106 measures the density of the sample 105 throughout an entirety of the testing time duration. In some implementations, the heater 108 is an electric heater (for example, an electric heating coil wrapped around the sample housing 104) that produces heat in response to receiving power. In some implementations, the heater 108 includes a heating jacket (for example, wrapped around the sample housing 104) through which a heating fluid is circulated (for example, heated oil or steam). The heater 108 can provide uniform heating to the sample 105 to maintain the sample 105 within the sample housing 104 at the specified temperature throughout the entirety of the testing time duration. The specified temperature can be in a range of from about 75 degrees Fahrenheit (° F.) to about 180° F. For example, the specified temperature can be in a range of from about 75° F. to about 80° F. In some implementations, the heater 108 is communicatively coupled to the computer 300. In such implementations, the computer 300 can control the heater 108. For example, the computer 300 can transmit a heating signal to the heater 108 to maintain the sample 105 within the sample housing 104 at the specified temperature throughout the entirety of the testing time duration.

Figure 1B:
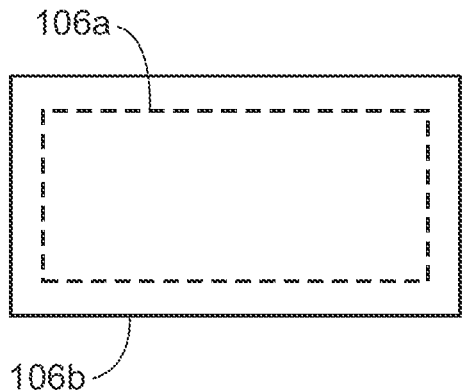
FIG. 1B is a side view of an example sensor that can be implemented in the system of FIG. 1A.
Figure 1C:
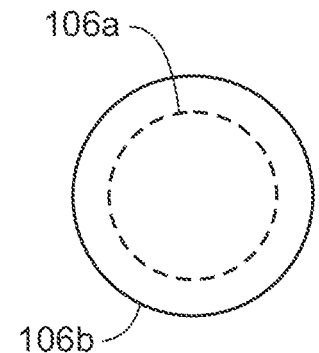
FIG. 1C is a front view of the sensor of FIG. 1B.
Figure 1D:
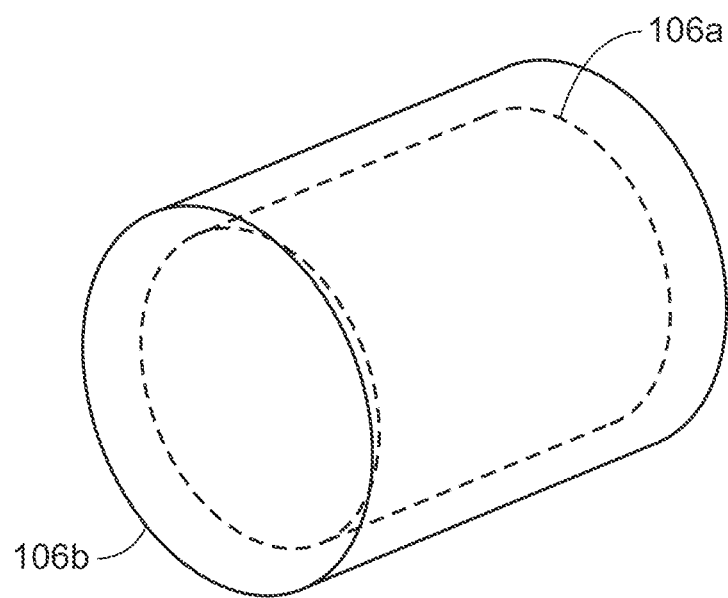
FIG. 1D is a perspective view of the sensor of FIG. 1B.

FIGS. 1B, 1C, and 1D depict a side view, a front view, and a perspective view, respectively, of an implementation of the cylindrical sensor 106. In some implementations, as shown in FIGS. 1B, 1C, and 1D, the cylindrical sensor 106 includes a core 106a. The core 106a can be encapsulated by a coating 106b. The core 106a and the coating 106b can be made of different materials. For example, the core 106a can be made of metal (such as platinum or stainless steel) or silica (such as glass). In implementations in which the cylindrical sensor 106 includes the core 106a and the coating 106b, the coating 106b is made of the fluoropolymer. The coating 106b can have a thickness of at least about 1 millimeter.

Figure 2:
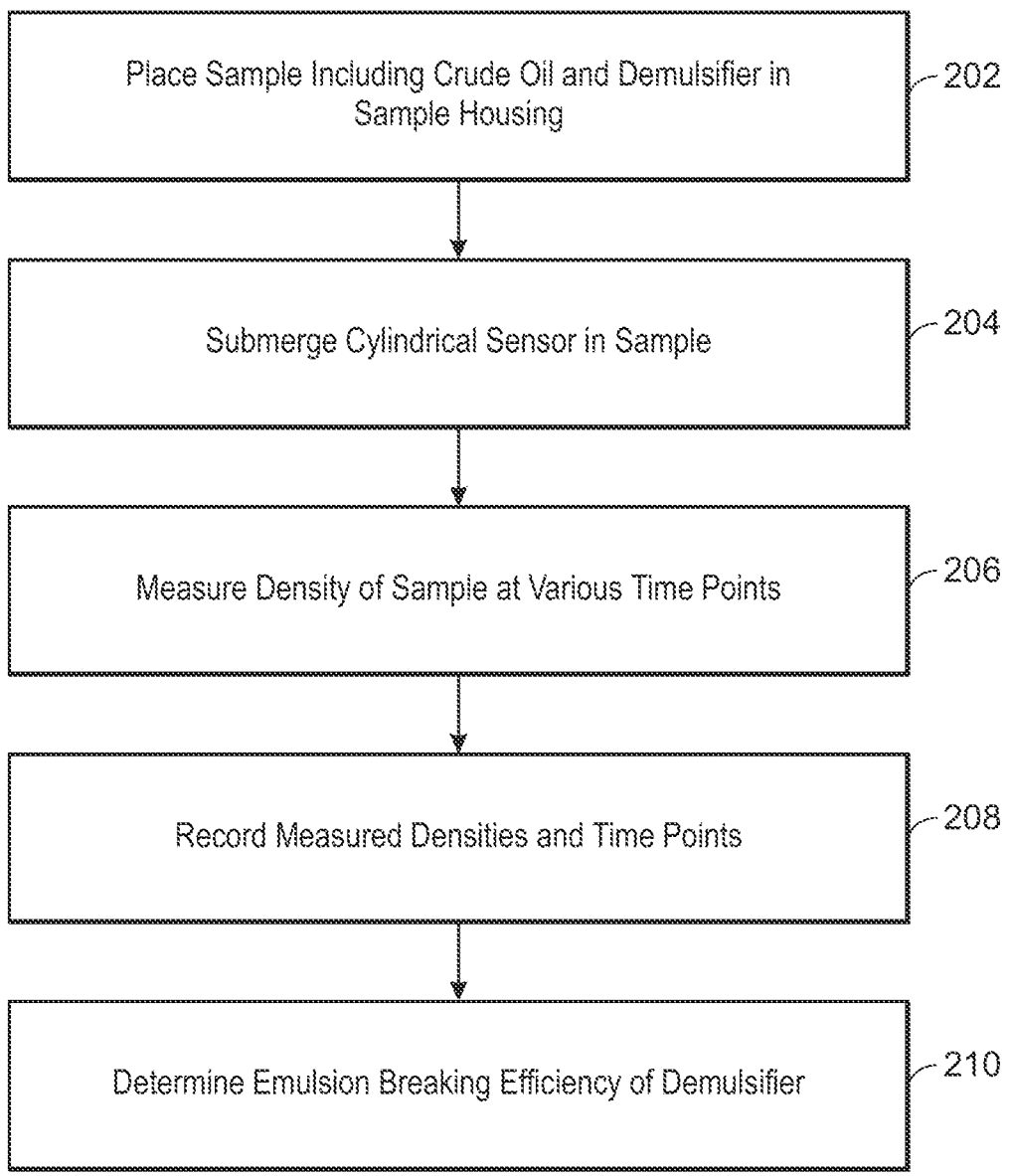
FIG. 2 is a flow chart of an example method for testing a demulsifier of crude oil.

FIG. 2 is a flow chart of an example method 200 for testing a demulsifier of crude oil. The method 200 can be implemented, for example, by the system 100. At block 202, a sample (such as the sample 105) is placed in a sample housing (such as the sample housing 104). As mentioned previously, the sample 105 includes crude oil and the demulsifier that is to be tested. The sample 105 can be prepared, for example, by stirring the crude oil and the demulsifier at a specified stirring rate and for a specified stirring time duration to form the sample 105 prior to placing the sample 105 in the sample housing 104 at block 202. The specified stirring rate for preparing the sample 105 is sufficient to adequately mix the crude oil and the demulsifier together without producing swirling. In some implementations, the specified stirring rate is in a range of from about 50 revolutions per minute (rpm) to about 400 rpm, from about 100 rpm to about 300 rpm, or from about 150 rpm to about 250 rpm. For example, the specified stirring rate is about 200 rpm. In some implementations, the specified stirring time duration is in a range of from about 30 seconds to about 360 seconds, from about 60 seconds to about 180 seconds, or from about 100 seconds to about 140 seconds. For example, the specified stirring time duration is about 120 seconds. In some implementations, the sample 105 is allowed to rest for a specified resting time after the sample 105 is placed in the sample housing 104 at block 202 before proceeding to block 204. The specified resting time can be, for example, less than 5 seconds, less than 4 seconds, less than 3 seconds, less than 2 seconds, or less than 1 second. In some implementations, the sample 105 is not allowed to rest after the sample 105 has been placed in the sample housing 104 at block 202, and the method immediately proceeds to block 204. At block 204, a cylindrical sensor (such as the cylindrical sensor 106) is submerged in the sample 105 within the sample housing 104. As mentioned previously, the external surface of the cylindrical sensor 106 includes a fluoropolymer, and the cylindrical sensor 106 has a density that is greater than the sample 105. At block 206, the density of the sample 105 is measured by a computer (such as the computer 300) that is communicatively coupled to the cylindrical sensor 106. The density of the sample 105 can be measured by the computer 300 multiple times at various time points over a specified testing time duration at block 206. At block 208, the density of the sample 105 measured at block 206 is recorded by the computer 300 (for example, to its memory). All of the densities measured at the various time points over the specified testing time duration at block 206 can be recorded by the computer 300 at block 208. Further, the densities can be matched with their respective time points (at which they were recorded), and the time points can also be recorded by the computer 300 at block 208. In some implementations, the sample 105 is maintained at a specified temperature throughout the entirety of the testing time duration (block 206). The sample 105 can be maintained at the specified temperature, for example, by the heater 108. At block 210, an emulsion breaking efficiency of the demulsifier is determined based on the recorded densities and corresponding time points. For example, the behavior of the change in density of the sample 105 over time can be analyzed to determine the emulsion breaking efficiency of the demulsifier at block 210. In some implementations, the computer 300 displays a plot of the densities versus corresponding time points (recorded at block 208), and the curve behavior of the plot is analyzed to determine the emulsion breaking efficiency of the demulsifier at block 210. Water has a greater density in comparison to oil, thus a demulsifier that causes the measured density of the sample 105 to decrease quickly can be deemed as a demulsifier with good performance. In some cases, demulsifier performance is determined by the extent at which the measured density of the sample 105 decreases during the test. A smaller density signifies better demulsifier performance. The "clean" oil phase of demulsified crude oil in which the oil and water phases have been appropriately separated by a demulsifier can have a density of about 0.867 $g/cm^3$. In some cases, demulsifier performance is determined by the time duration that it takes for the measured density of the sample 105 to reach the clean oil phase density. A shorter time duration signifies better demulsifier performance. In some cases, demulsifier performance is determined by both the decrease in density and the time duration it takes to reach the decreased density measurement.

FIG. 3 is a block diagram of an example computer 300 used to provide computational functionalities associated with described algorithms, methods, functions, processes, flows, and procedures, as described in this specification, according to an implementation. The illustrated computer 300 is intended to encompass any computing device such as a server, desktop computer, laptop/notebook computer, one or more processors within these devices, or any other processing device, including physical or virtual instances (or both) of the computing device. Additionally, the computer 300 can include a computer that includes an input device, such as a keypad, keyboard, touch screen, or other device that can accept user information, and an output device that conveys information associated with the operation of the computer 300, including digital data, visual, audio information, or a combination of information.

The computer 300 includes an interface 304. Although illustrated as a single interface 304 in FIG. 3, two or more interfaces 304 may be used according to particular needs, desires, or particular implementations of the computer 300. Although not shown in FIG. 3, the computer 300 can be communicably coupled with a network. The interface 304 is used by the computer 300 for communicating with other systems that are connected to the network in a distributed environment. Generally, the interface 304 comprises logic encoded in software or hardware (or a combination of software and hardware) and is operable to communicate with the network. More specifically, the interface 304 may comprise software supporting one or more communication protocols associated with communications such that the network or interface's hardware is operable to communicate physical signals within and outside of the illustrated computer 300. The interface 304 can include a control interface, which can be used to couple the computer 300 to controls. In some implementations, the control interface is a bank of relays, a bank of MOSFET power controllers, a serial peripheral interface (SPI), or a Fieldbus, and the like. The interface 304 can include a sensor interface, which can be used to couple the computer 300 to sensors, such as the cylindrical sensor 106. In some implementations, the sensor interface is a Universal Serial Bus (USB), a bank of analog-to-digital converters (ADCs), a I2C bus, a serial peripheral interface (SPI) bus, or a Fieldbus, and the like. The interface 304 can include a human machine interface, which can be used by a user to interact with the computer 300. In some implementations, the human machine interface includes a monitor or a touch screen that is configured to display information, for example, to a user.

The computer 300 includes a processor 305. The processor 305 may be a microprocessor, a multi-core processor, a multithreaded processor, an ultra-low-voltage processor, an embedded processor, or a virtual processor. In some embodiments, the processor 305 may be part of a system-on-a-chip (SoC) in which the processor 305 and the other components of the computer 300 are formed into a single integrated electronics package. In some implementations, the processor 305 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used. Although illustrated as a single processor 305 in FIG. 3, two or more processors may be used according to particular needs, desires, or particular implementations of the computer 300. Generally, the processor 305 executes instructions and manipulates data to perform the operations of the computer 300 and any algorithms, methods, functions, processes, flows, and procedures as described in this specification. The processor 305 may communicate with other components of the computer 300 over a bus. The bus may include any number of technologies, such as industry standard architecture (ISA), extended ISA (EISA), peripheral component interconnect (PCI), peripheral component interconnect extended (PCIx), PCI express (PCIe), or any number of other technologies. The bus may be a proprietary bus, for example, used in an SoC based system. Other bus technologies may be used, in addition to, or instead of, the technologies above.

The computer 300 can also include a data store 306 that can be used for long-term storage of programs and data. The data store 306 can be used for persistent storage of information, such as data, applications, operating systems, and so forth for the computer 300 or other components (or a combination of both) that can be connected to the network. Although illustrated as a single data store 306 in FIG. 3, two or more data stores (of the same or combination of types) can be used according to particular needs, desires, or particular implementations of the computer 300 and the described functionality. While data store 306 is illustrated as an integral component of the computer 300, data store 306 can be external to the computer 300. The data store 306 can be used for the persistent storage of information, such as data, applications, operating systems, and so forth. The data store 306 may be a nonvolatile RAM, a solid-state disk drive, or a flash drive, among others. In some implementations, the data store 306 will include a hard disk drive, such as a micro hard disk drive, a regular hard disk drive, or an array of hard disk drives, for example, associated with a DCS or a cloud server.

The computer 300 also includes a memory 307 that can hold data for the computer 300 or other components (or a combination of both) that can be connected to the network. Although illustrated as a single memory 307 in FIG. 3, two or more memories 307 (of the same or combination of types) can be used according to particular needs, desires, or particular implementations of the computer 300 and the described functionality. While memory 307 is illustrated as an integral component of the computer 300, memory 307 can be external to the computer 300. The memory 307 can be a transitory or non-transitory storage medium. In some implementations, such as in PLCs and other process control units, the memory 307 is integrated with the database 306 used for long-term storage of programs and data. The memory 307 can include any number of volatile and nonvolatile memory devices, such as volatile random-access memory (RAM), static random-access memory (SRAM), flash memory, and the like. In smaller devices, such as PLCs, the memory 307 may include registers associated with the processor 305 itself.

The memory 307 and/or the data store 306 stores computer-readable instructions executable by the processor 305 that, when executed, cause the processor 305 to perform operations, such as receiving the measured densities of the sample 105 from the cylindrical sensor 106 (block 308), attributing the measured densities to corresponding time points over the specified testing time duration (block 309), and recording the measured densities and corresponding time points to the memory 307 (block 310). The computer 300 can also include a power supply 314. The power supply 314 can include a rechargeable or non-rechargeable battery that can be configured to be either user- or non-user-replaceable. The power supply 314 can be hard-wired. There may be any number of computers 300 associated with, or external to, a computer system containing computer 300, each computer 300 communicating over the network. Further, the term "client," "user," "operator," and other appropriate terminology may be used interchangeably, as appropriate, without departing from this specification. Moreover, this specification contemplates that many users may use one computer 300, or that one user may use multiple computers 300.

Figure 4:
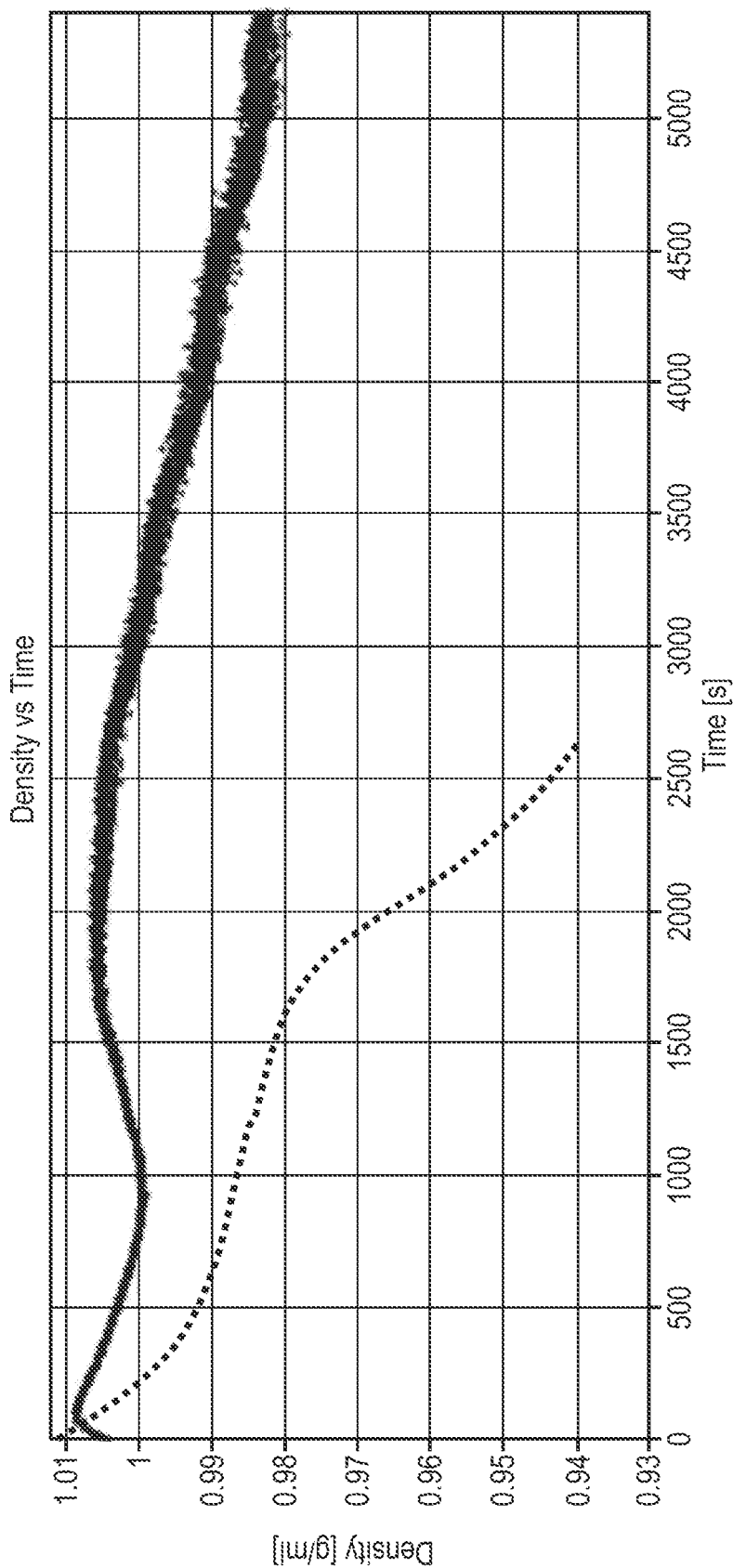
FIG. 4 is a plot of data for two experimental runs of testing different demulsifiers of crude oil.

FIG. 4 is an example plot 400 of densities versus time for two experimental runs of testing different demulsifiers. The solid curve provides density vs. time data for a first crude oil sample including a first demulsifier. The dotted curve provides density vs. time data for a second crude oil sample including a second demulsifier. The first crude oil sample included 100 parts per million (ppm) of the first demulsifier. The second crude oil sample included 100 ppm of the second demulsifier. Both samples were stirred at the same stirring rate and for the same stirring time duration. Both samples were also allowed to rest for the same resting time duration before density measurements were taken. As shown by the plot 400, the sample including the second demulsifier (dotted line) experienced a quicker decrease in density in comparison to the sample including the first demulsifier (solid line). Thus, the second demulsifier can be determined to have a greater emulsion breaking efficiency in comparison to the first demulsifier.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method comprising:
   placing a sample comprising crude oil and a demulsifier in a sample housing;
   submerging a cylindrical sensor in the sample within the sample housing, wherein an external surface of the cylindrical sensor comprises a fluoropolymer;
   measuring, by a computer communicatively coupled to the cylindrical sensor, a plurality of densities of the sample for a corresponding plurality of time points over a specified testing time duration;
   recording, by the computer, the plurality of densities and the corresponding plurality of time points; and
   determining an emulsion breaking efficiency of the demulsifier based on the recorded plurality of densities and corresponding plurality of time points.

2. The method of claim 1, wherein the fluoropolymer is polytetrafluoroethylene.

3. The method of claim 2, wherein the entire cylindrical sensor is made of the fluoropolymer.

4. The method of claim 2, wherein the cylindrical sensor comprises a core, and an entire external surface of the core is coated by the fluoropolymer.

5. The method of claim 4, wherein the fluoropolymer coating the entire external surface of the core has a thickness of about 1 millimeter.

6. The method of claim 5, comprising displaying, by the computer, a plot of the plurality of densities versus the corresponding plurality of time points.

7. The method of claim 6, comprising stirring the crude oil and the demulsifier at a specified stirring rate and for a specified stirring time duration to form the sample prior to placing the sample in the sample housing.

8. The method of claim 7, comprising allowing the sample to rest for a specified resting time duration after placing the sample in the sample housing and prior to submerging the cylindrical sensor in the sample within the sample housing.

9. The method of claim 8, comprising maintaining the sample at a specified temperature in a range of from about 75 degrees Fahrenheit (° F.) to about 180° F. while measuring the plurality of densities throughout an entirety of the testing time duration.

10. The method of claim 9, wherein the specified temperature is in a range of from about 75° F. to about 80° F.

11. A system comprising:
    a tensiometer comprising:
      a sample housing configured to hold a sample of crude oil and a demulsifier; and
      a cylindrical sensor configured to be placed within the sample housing and submerged in the sample, wherein an external surface of the cylindrical sensor comprises a fluoropolymer, the cylindrical sensor configured to, while submerged in the sample, measure a density of the sample; and
    a computer communicatively coupled to the cylindrical sensor, the computer comprising:
      a processor; and
      a computer-readable storage medium coupled to the processor and storing programming instructions for execution by the processor, the programming instructions instructing the processor to perform operations comprising:
        receiving a plurality of measured densities of the sample from the cylindrical sensor;
        attributing the plurality of measured densities to a corresponding plurality of time points over a specified testing time duration; and
        recording the plurality of measured densities of the sample and the corresponding plurality of time points to the computer-readable storage medium.

12. The system of claim 11, wherein the fluoropolymer is polytetrafluoroethylene.

13. The system of claim 12, wherein the entire cylindrical sensor is made of the fluoropolymer.

14. The system of claim 12, wherein the cylindrical sensor comprises a core, and an entire external surface of the core is coated by the fluoropolymer.

15. The system of claim 14, wherein the fluoropolymer coating the entire external surface of the core has a thickness of about 1 millimeter.

16. The system of claim 15, wherein the computer comprises an interface, and the operations comprise displaying, by the interface, a plot of the plurality of densities versus the corresponding plurality of time points.

17. The system of claim 16, wherein the tensiometer comprises a heater coupled to the sample housing and communicatively coupled to the computer.

18. The system of claim 17, wherein the operations comprise transmitting a heating signal to the heater to maintain the sample within the sample housing at a specified temperature while the cylindrical sensor measures the plurality of densities throughout an entirety of the testing time duration.

19. The system of claim 18, wherein the specified temperature is in a range of from about 75 degrees Fahrenheit (° F.) to about 180° F.

20. The system of claim 19, wherein the specified temperature is in a range of from about 75° F. to about 80° F.

* * * * *